United States Patent [19]

Michaux

[11] 4,163,697
[45] Aug. 7, 1979

[54] PROCESS FOR OBTAINING ISOBUTYLENE OF A PURITY HIGHER THAN 99.5 WEIGHT PERCENT

[75] Inventor: Jean-Pierre Michaux, Chatou, France

[73] Assignee: Compagnie Francaise de Raffinage, France

[21] Appl. No.: 769,738

[22] Filed: Feb. 17, 1977

[30] Foreign Application Priority Data

Feb. 27, 1976 [FR] France .................. 76 05649

[51] Int. Cl.² .................. B01D 1/14; B01D 3/06; C07C 7/04; C07C 7/10
[52] U.S. Cl. .................. 203/49; 203/71; 203/73; 203/80; 203/88; 585/811; 585/859
[58] Field of Search .................. 203/80, 49, 71, 73, 203/88, 43, 44, 46; 260/677 S, 677 A

[56] References Cited

U.S. PATENT DOCUMENTS

| 2,443,245 | 6/1948 | Hibshman ................. | 260/677 S |
| 2,509,885 | 5/1950 | Rupp et al. ................. | 260/677 S |
| 2,560,362 | 7/1951 | Morrell et al. ................. | 260/677 S |
| 3,073,874 | 1/1963 | Valet et al. ................. | 260/677 S |
| 3,150,201 | 9/1964 | Edwards et al. ................. | 260/677 S |
| 3,272,886 | 9/1966 | Edwards et al. ................. | 260/677 S |
| 3,544,653 | 12/1970 | Webb et al. ................. | 260/677 S |
| 3,794,690 | 2/1974 | Steggerda ................. | 260/677 S |

OTHER PUBLICATIONS

Martel et al.: Chemical Engineering Progress, vol. 61, No. 3, (Mar. 1965), pp. 77–80.

*Primary Examiner*—Wilbur L. Bascomb, Jr.
*Attorney, Agent, or Firm*—Curtis, Morris & Safford

[57] ABSTRACT

An improved process for recovering isobutylene contained in a mixture of hydrocarbons having four carbon atoms by selective extraction with an aqueous solution of sulfuric acid of a concentration of about 50 wt. % followed by separating the isobutylene-rich sulfuric acid extract by a first flash distillation of the extract and by a second physical separation of the isobutylene-enriched extract from said flashing step (which the latter physical separation is preferaby a second flash distillation at a temperature which is higher than the first and is at 75° C. or less, and wherein said first flash distillation is between 10° and 60° C. and both distillations are preferably at a pressure between 0.5 and 1.5 bars absolute to give an isobutylene purity greater than 99.5%).

20 Claims, 3 Drawing Figures

PROCESS FOR OBTAINING ISOBUTYLENE OF A PURITY HIGHER THAN 99.5 WEIGHT PERCENT

The present invention relates to a process for obtaining isobutylene by extraction with an aqueous solution of sulfuric acid, said process making it possible to obtain isobutylene of a purity higher than 99.5 wt. %.

The mixtures of hydrocarbons, having four carbon atoms obtained particularly in catalytic or steam cracking units in addition to isobutylene, contain hydrocarbons whose boiling temperature is close to that of isobutylene and which it is difficult to separate by superfractionation, particularly 1-butene.

It is already known to separate the isobutylene by selective extraction.

Thus the applicant's assignee has developed a process for the selective extraction of isobutylene contained in a mixture of hydrocarbons having four carbon atoms, said process comprising successively:

(a) A stage of extraction of the isobutylene from the mixture of hydrocarbons having four carbon atoms with an aqueous solution of sulfuric acid of a concentration of about 50 wt. %. In this extraction stage, the isobutylene on the one hand reacts with the sulfuric acid to form a sulfate and on the other hand is hydrolized to tertiary butyl alcohol. This extraction thus yields a sulfuric acid extract high in isobutylene content, the isobutylene being in the form of a sulfate, and tertiary butyl alcohol as well as a raffinate containing the major portion of the hydrocarbons having four carbon atoms, other than isobutylene, contained in the charge.

(b) A stage of separation of the isobutylene-rich sulfuric acid extract from the hydrocarbons having four carbon atoms still dissolved in said extract by subjecting said extract to flashing under reduced pressure.

(c) A stage of regeneration of the isobutylene by heating of the sulfuric acid extract, yielding a mixture of isobutylene, tertiary butyl alcohol, and polymers of isobutylene.

(d) A stage of washing the mixture obtained in the preceding stage with soda for elimination of the sulfuric acid still contained in the mixture.

(e) A stage of separation of the isobutylene contained in the mixture of isobutylene, tertiary butyl alcohol, and polymers of isobutylene.

This process has been described particularly in Chemical Engineering Progress, vol. 61, No. 3 (March 1965), pp. 77-80.

This process offers the great advantage of permitting extraction and regeneration of the isobutylene by the use of a sulfuric acid solution of constant concentration, thus eliminating the successive dilutions and reconcentrations of the sulfuric acid solutions necessary in the previous processes for extraction with sulfuric acid, which used sulfuric acid solutions of a concentration of about 60 to 70 wt. % for the extraction.

The foregoing process, which for greater clarity will be described below partly with reference to FIG. 1 of the three accompanying drawings, makes it possible to obtain isobutylene of a purity of up to 99.5 wt. %.

Assignee's copending application Serial No. 683,178, filed May 4, 1976, now issued as U.S. Pat. No. 4,108,843 on Apr. 19, 1977, teaches the apparently first commercially practical method of improving the foregoing method to a purity of above 99.5 wt. %.

The extraction and separation phases of the isobutylene extraction process referred to above will now be described with reference to FIG. 1.

A charge consisting essentially of hydrocarbons having four carbon atoms and containing particularly isobutylene is introduced into the isobutylene extraction unit through line 1. An aqueous solution of sulfuric acid of a concentration of about 50 wt. % is also introduced into the unit, through line 2.

The charge and the sulfuric acid solution are conducted through line 3 to a centrifugal pump 4.

The mixture formed is piped through line 5 to a heat exchanger 6. The reaction between the isobutylene and the sulfuric acid being exothermic, it is necessary to lower the temperature of the mixture before it is introduced through line 7 into the upper part of a reactor 8.

Figure 1:
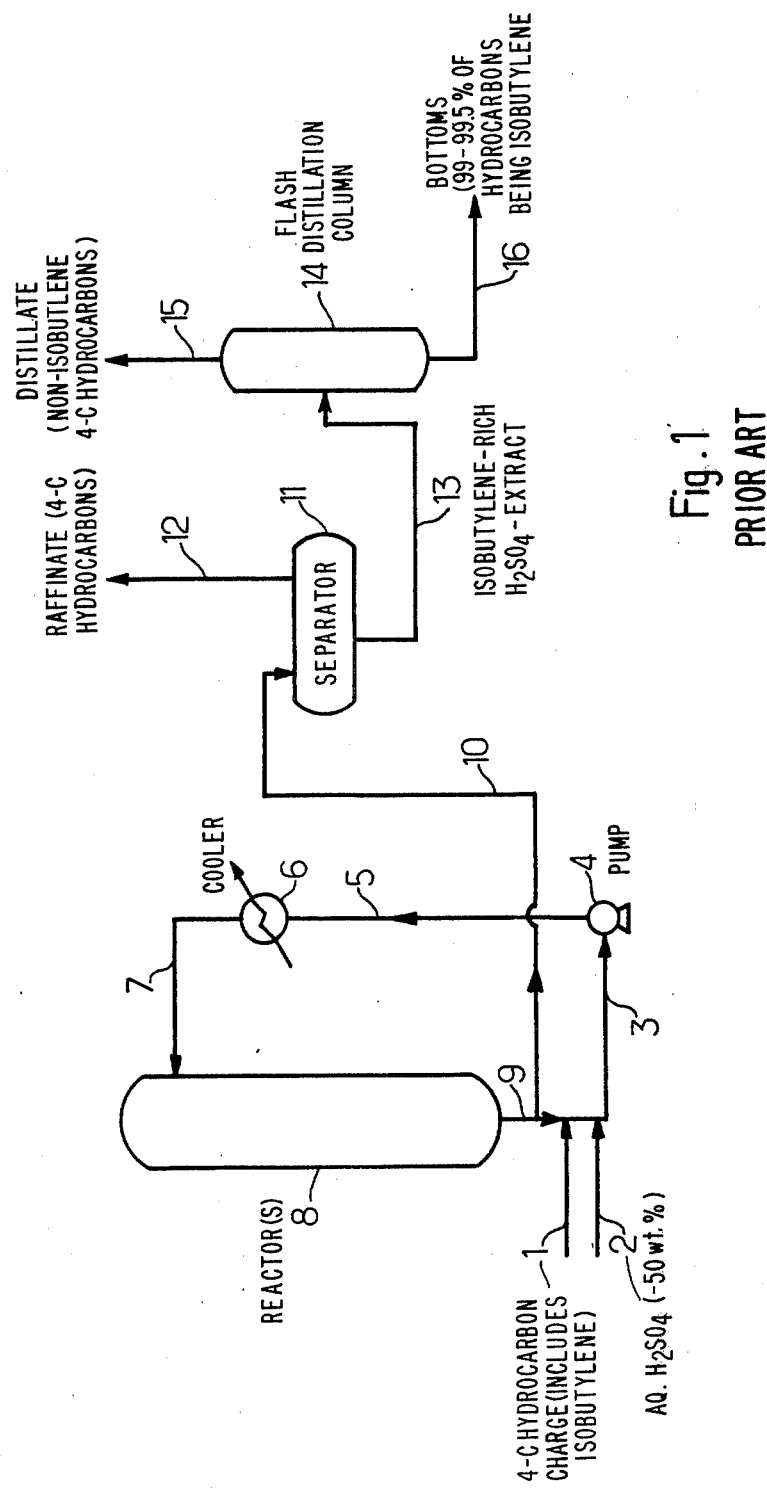
FIG. 1 is a simplified flow diagram of the stages of extraction of the isobutylene and of separation of the sulfuric acid extract and the hydrocarbons having four carbon atoms in a unit employing the unimproved isobutylene extraction process described in the aforementioned Chemical Engineering Progress article.

While only one reactor is shown in FIG. 1, there may be several reactors.

The pressure inside the reactor may be comprised between 6 and 15 bars absolute, and the temperature between 10° and 60° C.

The sulfuric acid extract high in isobutylene content, which further contains, in solution, hydrocarbons other than isobutylene having four carbon atoms, tertiary butyl alcohol, and hydrocarbons other than isobutylene having four carbon atoms not dissolved in the sulfuric acid, are collected at the base of the reactor 8 through line 9.

A portion of this effluent collected through line 9 is recycled to the reactor 8 through line 3 while another portion is conducted through line 10 to the separator 11.

At the top of separator 11, through line 12, a raffinate is collected which consists of the hydrocarbons having four carbon atoms which have not been dissolved in the sulfuric acid, such as the normal butenes, butadiene and isobutylene as well as polymers of isobutylene having from 8 to 12 carbon atoms, and tertiary butyl alcohol.

This raffinate is piped to washing apparatus (not shown) using soda and then water for removal of the sulfuric acid which it contains.

The sulfuric acid extract rich in isobutylene, which still contains a small proportion of dissolved hydrocarbons, is collected at the base of separator 11 through line 13. This extract is conducted to the middle part of a flash distillation column 14.

The pressure in the interior of that column is less than 1 bar absolute, and the temperature is substantially the same as that of reactor 8.

The major portion of the hydrocarbons having four carbon atoms, other than isobutylene, dissolved in the sulfuric acid extract introduced into column 14 through line 13 is collected as a distillate at the top of column 14 through line 15. These hydrocarbons may be recycled to the charge or conducted to the raffinate after compression and condensation of the gases.

The extract rich in isobutylene, which still contains from 0.5 to 1 wt. %, based on the isobutylene, of hydrocarbons having four carbon atoms, is collected as bottoms at the base of column 14 through line 16.

This rich extract is then treated in known manner, as described in the article in Chemical Engineering Progress cited earlier, to yield isobutylene of a purity of up to 99.5 wt. %.

In pursuing his work, the applicant has found that it is possible to increase the purity of the isobutylene obtained still further. When the sulfuric acid extract high in isobutylene content and the hydrocarbons having four carbon atoms dissolved in the extract are separated by flashing under reduced pressure, not all of these hydrocarbons are separated. Some of them remain in the extract, which diminishes the final purity of the isobutylene obtained.

It has occurred to the applicant that this drawback may be overcome by effecting said separation in two steps.

A purpose of the present invention thus is to improve the process described above with a view to increasing the purity of the isobutylene obtained.

Therefore a preferred embodiment of the present invention is an improved process for recovering the isobutylene contained in a mixture of hydrocarbons containing four carbon atoms by selective extraction with an aqueous solution of sulfuric acid of a concentration of about 50 wt. %, said process being characterized in that the stage of separation of the sulfuric acid extract rich in isobutylene and of the hydrocarbons having four carbon atoms still dissolved in said extract comprises at least two successive steps, the first step consisting of subjecting said rich extract to flashing while the second step comprises subjecting the isobutylene-enriched extract obtained at the end of the first step to a physical separation.

With reference to FIG. 1, the process in accordance with the invention thus consists in subjecting the rich sulfuric acid extract collected through line 13 to a two-step separation of the dissolved hydrocarbons.

The rich extract is separated in a first step from the major portion of the hydrocarbons having four carbons dissolved in the sulfuric acid.

Said first separation step consists in a flashing operation at a pressure which may, for example, be comprised between 0.5 and 4 bars absolute, and preferably between 0.5 and 1.5 bars absolute, and at a temperature close to that which prevails in the extraction-stage reactor operating at the highest temperature.

The enriched extract so obtained is then passed through a second separation step, the purpose of which is to separate the hydrocarbons still dissolved in the rich extract.

This second step may consist of a second flashing operation at a pressure which may be comprised between 0.5 and 1.5 bars absolute.

In said second step, the separation of the dissolved gases is further promoted:

(a) By bringing the rich extract to a temperature above that of the first separation step and which may be about 75° C. or less.

(b) By stripping the dissolved gases with a gas such as hydrogen, nitrogen, methane or a refinery gas composed mainly of hydrogen and methane.

(c) By combining the operations under (a) and (b).

The process in accordance with the present invention may be used to treat charges of hydrocarbons having four carbon atoms and containing from 10 to 60 wt. % of isobutylene.

It makes it possible to obtain isobutylene of a purity higher than 99.5 wt. %.

In addition to yielding isobutylene of a purity higher than 99.5 wt. %, the process in accordance with the present invention permits the raffinate to be depleted of isobutylene and a raffinate containing less than 2.5 wt. % of isobutylene to be obtained when an appropriate number of reactors is used.

More particularly, it permits a raffinate both rich in normal butenes and containing less than 2.5 wt. % of isobutylene to be obtained from a charge containing from 10 to 60 wt. % of isobutylene and from 20 to 50 wt. % of normal butenes.

Figure 2:
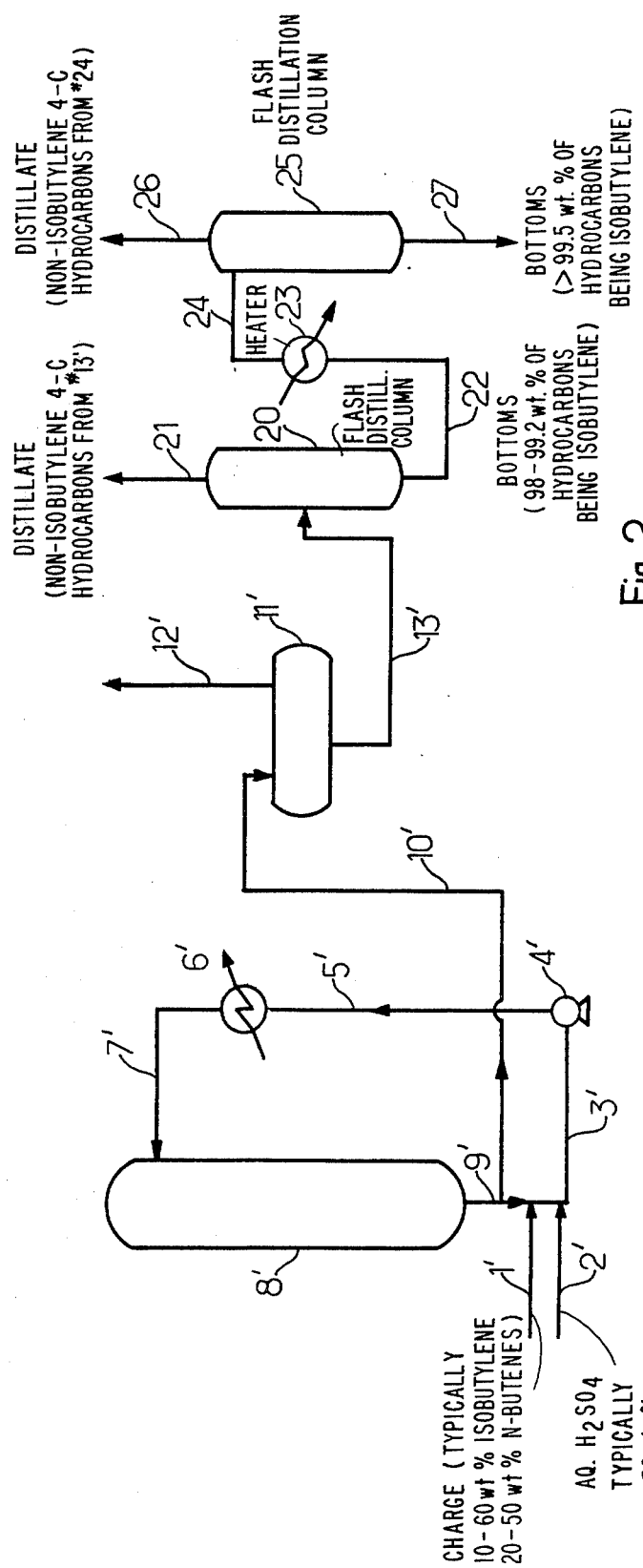
FIGS. 2 and 3 are simplified flow diagrams of two improved modifications of the stages of extraction of the isobutylene and of separation of the sulfuric acid extract and the hydrocarbons having four carbon atoms in a unit employing the process in accordance with the present invention, which yield isobutylene of a purity greater than 99.5%.
Figure 3:
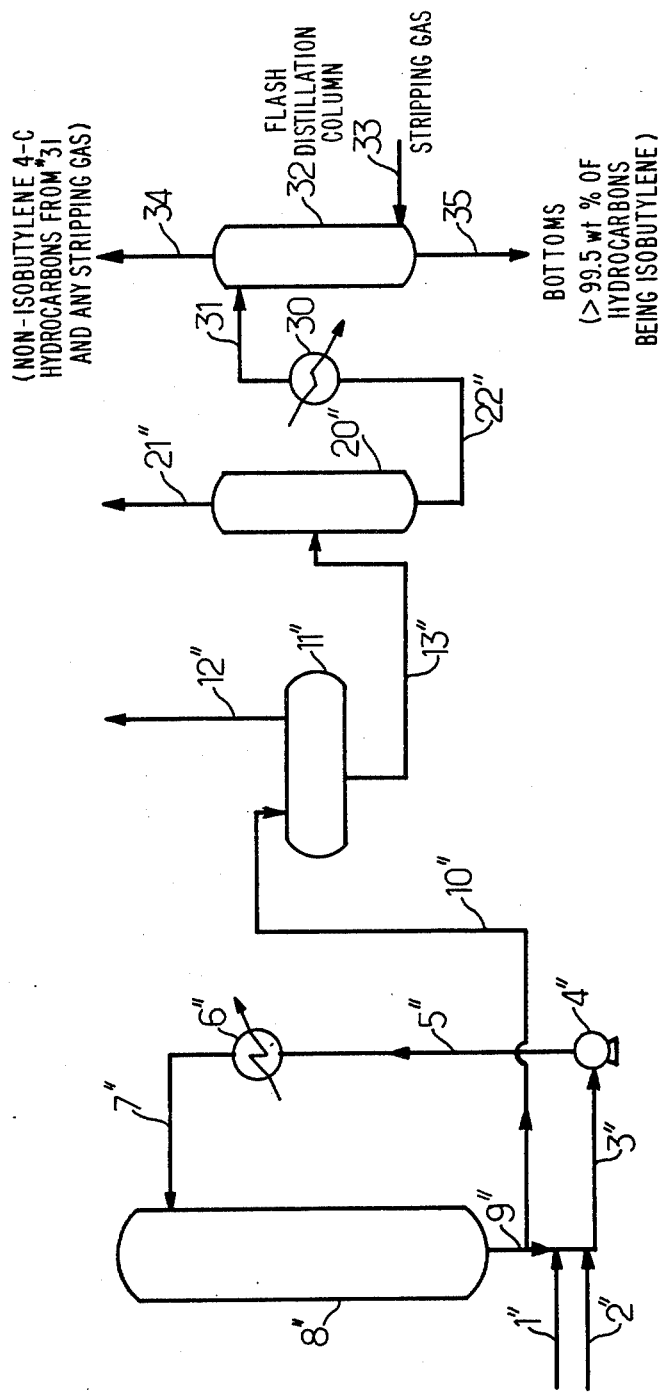

FIGS. 2 and 3, illustrate how the process in accordance with the present invention is practiced. Only the portions of these figures which differ from FIG. 1 will be described, the portions common to FIGS. 1 and 2 being designated in FIG. 2 by the same references as in FIG. 1 but suffixed with a prime (') while the portions of FIG. 3 which also occur in FIGS. 1 and 2 will retain the same references but suffixed with a double prime (").

The modes of practice of FIGS. 2 and 3 differ from each other in that stripping with a gas is provided for in FIG. 3 but not in FIG. 2.

With reference to FIG. 2, the extract high in isobutylene content collected through line 13' and still containing from 2 to 6 wt. %—based on the isobutylene, and depending on the proportion of solvent used for the extraction—of hydrocarbons having four carbon atoms is piped into the middle part of a flash distillation column 20.

The pressure in the interior of said column may be comprised between 0.5 and 4 bars absolute, and preferably between 0.5 and 1.5 bars absolute, and the temperature is substantially the same as that of reactor 8'.

At the top of column 20, the major portion of the hydrocarbons other than isobutylene having four carbon atoms which are dissolved in the sulfuric acid is collected as a distillate through line 21. These hydrocarbons may be recycled to the charge or conducted to the raffinate, after compression and condensation of the gases.

At the base of column 20, the bottoms (in the form of an isobutylene-rich extract containing from 0.8 to 2 wt. %, based on the isobutylene, of hydrocarbons having four carbon atoms) is collected through line 22. After passing through a reheater 23, this extract is piped into the middle part of a second flash distillation column 25.

The pressure in the interior of that column may be comprised between 0.5 and 1.5 bars absolute, and the temperature may be 75° C. or less.

At the top of column 25, the major portion of the hydrocarbons other than isobutylene having four carbon atoms dissolved in the sulfuric acid extract introduced into column 25 through line 24 is collected as a distillate through line 26. These hydrocarbons may be recycled to the charge or conducted to the raffinate, after compression and condensation of the gases.

At the base of column 25, the bottoms (in the form of an isobutylene-rich extract containing less than 0.5 wt. %, based on the isobutylene, of hydrocarbons having four carbon atoms) is collected through line 27.

This rich extract is then treated as described in the article in Chemical Engineering Progress cited earlier to yield isobutylene of a purity higher than 99.5 wt. %.

In the case of FIG. 3, the bottoms (in the form of an isobutylene-rich extract collected at the base of column 20" through line 22") is piped, possibly after being passed through a reheater 30, through line 31, into the middle part of a second flash distillation column 32.

The pressure in the interior of that column 32 may be

Temperature: 65° C.

The compositions of the principal lines of the units in tests A and B are given in Table I which follows.

Table I

| LINE<br>TEST<br>COMPOSITION | 1 or 1'<br>A or B<br>Wgt.(g) | Wt.% | 12 or 12'<br>A or B<br>Wgt.(g) | Wt.% | 15<br>A<br>Wgt.(g) | Wt.% | 21<br>B<br>Wgt.(g) | Wt.% | 26<br>B<br>Wgt.(g) | Wt.% |
|---|---|---|---|---|---|---|---|---|---|---|
| Hydrocarbons having three carbon atoms | 50 | 0.5 | 48.1 | 0.8 | 1.7 | 0.8 | 1.3 | 0.8 | 0.5 | 0.4 |
| Isobutane | 1100 | 11.0 | 1065.7 | 17.8 | 33.4 | 16.2 | 26.6 | 15.9 | 7.8 | 5.6 |
| n-Butane | 500 | 5.0 | 483.6 | 8.1 | 14.9 | 7.2 | 12.5 | 7.5 | 3.3 | 2.6 |
| 1-Butene | 2900 | 29.0 | 2814.7 | 47.1 | 78.0 | 37.6 | 66.7 | 40.0 | 17.3 | 13.4 |
| Isobutene | 4000 | 40.0 | 125.0 | 2.1 | 29.4 | 14.3 | 21.1 | 12.6 | 68.4 | 52.8 |
| 1,3-Butadiene | 50 | 0.5 | 47.2 | 0.8 | 2.1 | 1.0 | 1.9 | 1.1 | 0.7 | 0.5 |
| trans-2-Butene | 750 | 7.5 | 720.6 | 12.0 | 18.5 | 9.0 | 16.4 | 9.8 | 6.4 | 5.0 |
| cis-2-Butene | 650 | 6.5 | 626.7 | 10.5 | 16.0 | 7.8 | 13.9 | 8.3 | 4.3 | 3.3 |
| tert-Butyl alcohol | 0 | 0 | 22.0 | 0.35 | 10.9 | 45.3 | 5.8 | 3.5 | 18.0 | 13.9 |
| Isobutylene polymers | 0 | 0 | 28.1 | 0.45 | 0 | 0 | 0 | 0 | 0 | 0 |
| Water | 0 | 0 | 0 | 0 | 1.3 | 0.6 | 0.8 | 0.5 | 3.5 | 2.5 |
| Total | 10000 | 100 | 5981.7 | 100 | 206.2 | 100 | 167.0 | 100 | 129.5 | 100 | comprised between 0.5 and 1.5 bars absolute, and the temperature may be 75° C. or less.

A gas intended for stripping of the hydrocarbons having four carbon atoms dissolved in the sulfuric acid piped into column 32 through line 31 is introduced at the base of column 32 through line 33.

The feed rate of this gas is comprised between 2 and 10 normal liters (measured at 0° C. and under an absolute pressure of 1 atmosphere) per liter of sulfuric acid extract.

This gas and the stripped hydrocarbons are collected as a distillate at the top of column 32 through line 34. The isobutylene-rich extract containing less than 0.5 wt. %, based on the isobutylene, of hydrocarbons having four carbon atoms is collected as bottoms at the base of column 32 through line 35.

This rich extract is then treated as described in the article in Chemical Engineering Progress cited earlier to yield isobutylene of a purity higher than 99.5 wt. %.

The examples which follow illustrate the practice of the invention.

EXAMPLE 1

This example relates to tests A and B involving the treatment of identical charges of hydrocarbons having four carbon atoms.

Test A is performed for control purposes by a process analogous to that illustrated by FIG. 1, which is not the process in accordance with the invention.

Test B is performed by a process in accordance with the invention analogous to that illustrated in FIG. 2.

The operating parameters of the reactors 8 and 8' are the same for both test A and test B, namely:
Pressure: 8 bars absolute
Temperature: 40° C.

The operating parameters of column 14 (test A) are as follows:
Pressure: 0.8 bar absolute
Temperature: 40° C.

The operating parameters of columns 20 and 25 (test B) are as follows:
Column 20:
Pressure: 1.1 bar absolute
Temperature: 40° C.
Column 25:
Pressure: 0.6 bar absolute It is apparent from Table I that the separation of isobutylene from the other hydrocarbons having four carbon atoms is better in test B than in control test A.

For 1-butene, for example, the starting weight of the 1-butene in the charge in 2900 grams. The raffinate (line 12 or 12') contains 2814.7 g of 1-butene in the case of both test A and test B. Thus there is 85.3 g of 1-butene present in the isobutylene-rich extract (line 13 or 13').

In the case of test A, 78 g of 1-butene (line 15) is separated in the separation stage.

In the case of test B, 84 g of 1-butene (66.7 g in line 21 and 17.3 g on line 26) is separated in the separation stage.

The purity of the isobutylene obtained thus is better in the case of test B.

EXAMPLE 2

This example relates to tests C and D involving the treatment of identical charges of hydrocarbons having four carbon atoms.

Test C is performed for control purposes by a process analogous to that illustrated by FIG. 1, which is not the process in accordance with the invention.

Test D is performed by a process in accordance with the invention analogous to that illustrated by FIG. 3.

The operating parameters for reactors 8 and 8" are the same for both tests C and D, namely:
Pressure: 8 bars absolute
Temperature: 30° C.

The operating parameters of column 14 (test C) are as follows:
Pressure: 1 bar absolute
Temperature: 30° C.

The operating parameters of columns 20" and 32 (test D) are as follows:
Column 20":
Pressure: 1 bar absolute
Temperature: 30° C.
Column 32:
Pressure: 1 bar absolute
Temperature: 45° C.

The feed rate of the stripping gas, nitrogen, is 3.8 normal liters (measured at 0° C. and under an absolute pressure of 1 atmosphere) per liter of sulfuric acid introduced into column 32.

The compositions of the principal lines of the units in tests C and D are given in Table II which follows.

TABLE II

| LINE | 1 or 1" | | 12 or 12" | | 15 or 21" | | 34* | |
|---|---|---|---|---|---|---|---|---|
| TEST | C or D | | C or D | | C or D | | D | |
| COMPOSITION | Wgt. (g) | Wt. % | Wgt. (g) | Wt. % | Wgt. (g) | Wt. % | Wgt. (g) | Wt. % |
| Ethane | 1.27 | 0.13 | 1.21 | 0.16 | 0.03 | 0.44 | 0.03 | 0.21 |
| Propane | 21.16 | 2.12 | 20.85 | 2.76 | 0.25 | 3.69 | 0.06 | 0.43 |
| Propene | 4.49 | 0.45 | 4.36 | 0.58 | 0.09 | 1.33 | 0.00 | 0.21 |
| Isobutane | 6.92 | 0.69 | 6.86 | 0.91 | 0.04 | 0.59 | 0.02 | 0.14 |
| n-Butane | 12.35 | 1.23 | 12.25 | 1.62 | 0.07 | 1.08 | 0.08 | 0.21 |
| 1-Butene | 202.48 | 20.25 | 199.93 | 26.41 | 1.61 | 23.78 | 0.91 | 6.51 |
| Isobutene | 278.10 | 27.81 | 40.51 | 5.35 | 0.20 | 2.95 | 8.75 | 62.59 |
| 1,3-Butadiene | 369.70 | 36.97 | 362.25 | 47.86 | 3.70 | 54.66 | 3.55 | 25.40 |
| trans-2-Butene | 66.60 | 6.66 | 65.53 | 8.66 | 0.50 | 7.40 | 0.36 | 2.58 |
| cis-2-Butene | 33.30 | 3.33 | 32.77 | 4.33 | 0.25 | 3.69 | 0.18 | 1.29 |
| Pentanes | 3.63 | 0.36 | 3.55 | 0.47 | 0.02 | 0.29 | 0.06 | 0.43 |
| tert-Butyl alcohol | 0 | 0 | 4.53 | 0.60 | 0.01 | 0.15 | 0 | 0 |
| Isobutylene polymers | 0 | 0 | 2.20 | 0.29 | 0 | 0 | 0 | 0 |
| Water | 0 | 0 | 0 | 0 | 0 | 0 | 0 | 0 |
| Total | 1000.00 | 100.00 | 756.80 | 100 | 6.77 | 100.00 | 13.98 | 100.00 |

*The composition of line 34 is given without taking into account the stripping gas, for ease of comparison with the composition of line 12 or line 12".

It is apparent from Table II that the separation of isobutylene from the other hydrocarbons having four carbon atoms is better in test D than in control test C.

For 1-butene, for example, the starting weight of the 1-butene in the charge is 202.48 g. The raffinate (line 12 or 12") contains 199.93 g of 1-butene in the case of both test C and test D. Thus there remains 2.55 g of 1-butene in the isobutylene-rich extract (line 13 or 13").

In the case of test C, 1.61 g of 1-butene (line 15) is separated in the separation stage.

In the case of test D, 2.52 g of 1-butene (1.61 g in line 21" and 0.91 g in line 34) is separated in the speararion stage.

The purity of the isobutylene obtained thus is better in the case of test D.

I claim:

1. In a process for recovering isobutylene contained in a mixture of hydrocarbons having four carbon atoms, by selective liquid-liquid extraction with an aqueous solution of sulfuric acid of a concentration of about 50 wt. % to give an isobutylene-rich sulfuric acid extract which is then subjected to a flash distillation in a zone to further enrich the isobutylene content of said extract, the improvement for obtaining isobutylene of a purity of greater than 99.5 wt. % comprising removing the bottoms from said flash distillation zone, heating said separated bottoms to an effective distillation temperature and in a separate zone subjecting the heated bottoms to a further independent flashing step.

2. A process as defined in claim 1, further comprising carrying out the first flashing step at a temperature comprised between 10° and 60° C. and at a pressure between 0.5 and 4 bars absolute.

3. A process as defined in claim 2, wherein said pressure is between 0.5 and 1.5 bars absolute.

4. A process as defined in claim 2, further comprising carrying out the second step of the separation stage at a pressure between 0.5 and 1.5 bars absolute and at a temperature that is higher than that at which the first flashing step is carried out and is at 75° C. or less.

5. A process as defined in claim 2, further comprising simultaneously stripping the gases dissolved in the bottoms from the first flashing step with a stripping gas.

6. A process as defined in claim 4, wherein during the second flashing step the gases dissolved in the bottoms from the first flashing step are stripped with a stripping gas.

7. A process as defined in claim 5, wherein the stripping gas is selected from the group consisting of hydrogen, nitrogen, methane and a refinery gas.

8. A process as defined in claim 6, wherein the stripping gas is selected from the group consisting of hydrogen, nitrogen, methane and a refinery gas.

9. In the process defined in claim 1 said mixture of hydrocarbons having four carbon atoms comprising from 10 to 60 wt. % of isobutylene.

10. In the process defined in claim 4, to the treatment of a charge of hydrocarbons having four carbon atoms comprising from 10 to 60 wt. % of isobutylene.

11. In the process defined in claim 5 to the treatment of a charge of hydrocarbons having four carbon atoms comprising from 10 to 60 wt. % of isobutylene.

12. In the process defined in claim 5 to the treatment of a charge of hydrocarbons having four carbon atoms comprising from 10 to 60 wt. % of isobutylene and from 20 to 50 wt. % of normal butenes.

13. In the process defined in claim 4 to the treatment of a charge of hydrocarbons having four carbon atoms comprising from 10 to 60 wt. % of isobutylene and from 20 to 50 wt. % of normal butenes.

14. In a process for recovering isobutylene contained in a mixture of hydrocarbons having four carbon atoms, by selective liquid-liquid extraction with an aqueous solution of sulfuric acid of a concentration of about 50 wt. % to give an isobutylene-rich sulfuric acid extract which is then subjected to a flash distillation in a zone to further enrich the isobutylene content of said extract, the improvement for obtaining isobutylene of a purity of greater than 99.5 wt. % comprising removing the bottoms from said flash distillation zone, and independently stripping the gases dissolved in the bottoms from the first flashing step with a stripping gas.

15. A process as defined in claim 14, further comprising carrying out the first flashing step at a temperature comprised between 10° and 60° C. and at a pressure between 0.5 and 4 bars absolute.

16. In the process defined in claim 15 to the treatment of a charge of hydrocarbons having four carbon atoms comprising from 10 to 60 wt. % of isobutylene and from 20 to 50 wt. % of normal butenes.

17. In the process defined in claim 16, to the treatment of a charge of hydrocarbons having four carbon atoms comprising from 10 to 60 wt. % of isobutylene.

18. A process as defined in claim 13, wherein the stripping gas is selected from the group consisting of hydrogen, nitrogen, methane and a refinery gas.

19. In the process defined in claim 18, the feed rate of the stripping gas is between 2 and 10 normal liters (at standard temperature and pressure) per liter of sulfuric acid extract.

20. A process as defined in claim 16, wherein the stripping gas is selected from the group consisting of hydrogen, nitrogen, methane and a refinery gas.

* * * * *

UNITED STATES PATENT AND TRADEMARK OFFICE
CERTIFICATE OF CORRECTION

PATENT NO. : 4,163,697
DATED : August 7, 1979
INVENTOR(S) : Jean-Pierre Michaux

It is certified that error appears in the above-identified patent and that said Letters Patent are hereby corrected as shown below:

Column 8, claim 10, lines 32 to 33; claim 11, lines 35 to 36; claim 12, lines 38 to 39; claim 13, lines 42 to 43; claim 16, lines 62 and 63; and claim 17, lines 66 and 67; replace "to the treatment of a charge" by --said mixture--;

Column 8, claim 17, line 66, replace "16" by --15--; and

Column 9, claim 18, line 1, replace "13" by --17--.

Signed and Sealed this

Twenty-sixth Day of February 1980

[SEAL]

Attest:

SIDNEY A. DIAMOND

Attesting Officer   Commissioner of Patents and Trademarks